US00PP22356P3

(12) United States Plant Patent
White

(10) Patent No.: US PP22,356 P3
(45) Date of Patent: Dec. 20, 2011

(54) APPLE TREE NAMED 'PREMA17'

(50) Latin Name: ***Malus domestica* Mill.**
Varietal Denomination: PremA17

(75) Inventor: Allan G. White, Havelock North (NZ)

(73) Assignee: Prevar Limited, Hastings (NZ)

( * ) Notice: Subject to any disclaimer, the term of this patent is extended or adjusted under 35 U.S.C. 154(b) by 0 days.

(21) Appl. No.: 12/660,408

(22) Filed: Feb. 24, 2010

(65) Prior Publication Data

US 2010/0229267 P1 Sep. 9, 2010

Related U.S. Application Data

(60) Provisional application No. 61/208,862, filed on Feb. 26, 2009.

(51) Int. Cl.
*A01H 5/00* (2006.01)

(52) U.S. Cl. ..... Plt./161

(58) Field of Classification Search ..... Plt./161
See application file for complete search history.

*Primary Examiner* — June Hwu
(74) *Attorney, Agent, or Firm* — Ballew Law

(57) ABSTRACT

'PremA17' is a new and distinct apple tree (*Malus domestica* Mill.) notable for its attractive blush yellow color and excellent flavor and texture.

2 Drawing Sheets

Genus and species: *Malus domestica* Mill.
Variety denomination: 'PremA17'.

STATEMENT REGARDING FEDERALLY SPONSORED RESEARCH OR DEVELOPMENT

None:

BACKGROUND AND SUMMARY OF THE VARIETY

The new variety of apple tree 'PremA17' was created in the course of a planned breeding program carried out in Hawkes Bay, New Zealand. 'PremA17' originated as a result of a controlled cross of 'A045R13T007' (not patented, seed parent) and 'A020R02T167' (not patented, pollen parent). 'PremA17' was selected as a single plant from among a population of seedlings derived from the parents, and was selected for its attractive fruit and its excellent flavor and texture. It is distinguished from its parents by its early harvest season which in Hawkes Bay, New Zealand is the first week of February. A045R13T007 is harvested in late February or early March and A020R02T167 in the third week of February at the same time as 'Royal Gala'(U.S. Plant Pat. No. 4,121). Asexual propagation by budding was first carried out in Havelock North, New Zealand. The variety has since been observed over a number of asexually propagated generations, and has been found to remain true to type.

BRIEF DESCRIPTION OF THE PHOTOGRAPHS

Figure 1:
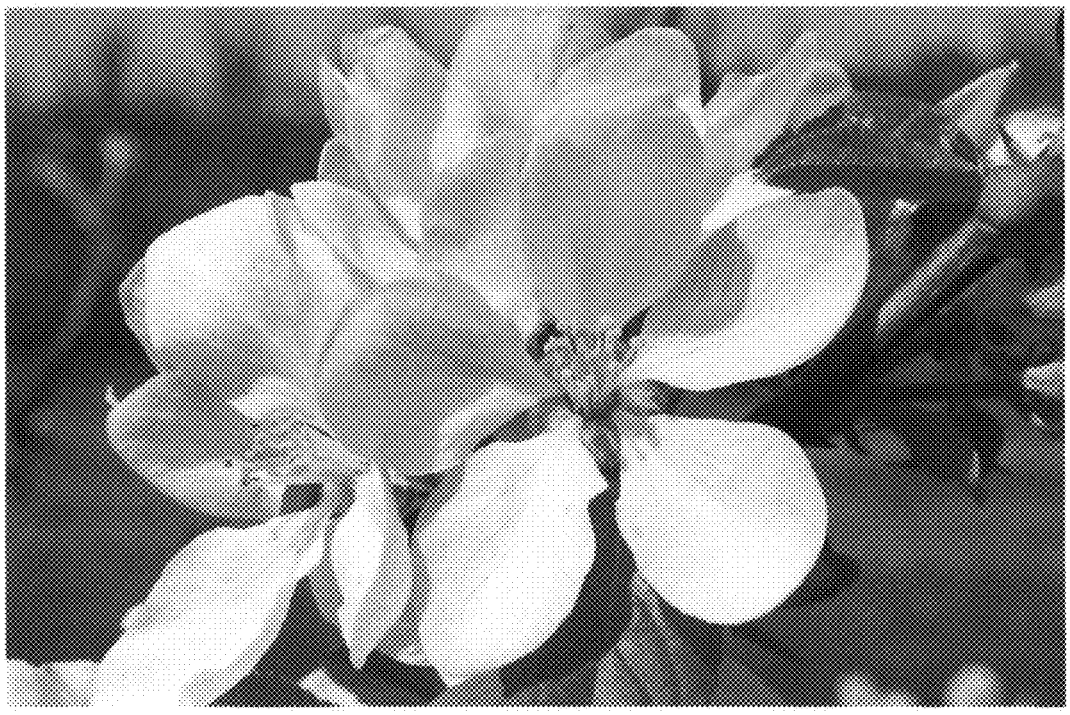
Figure 2:
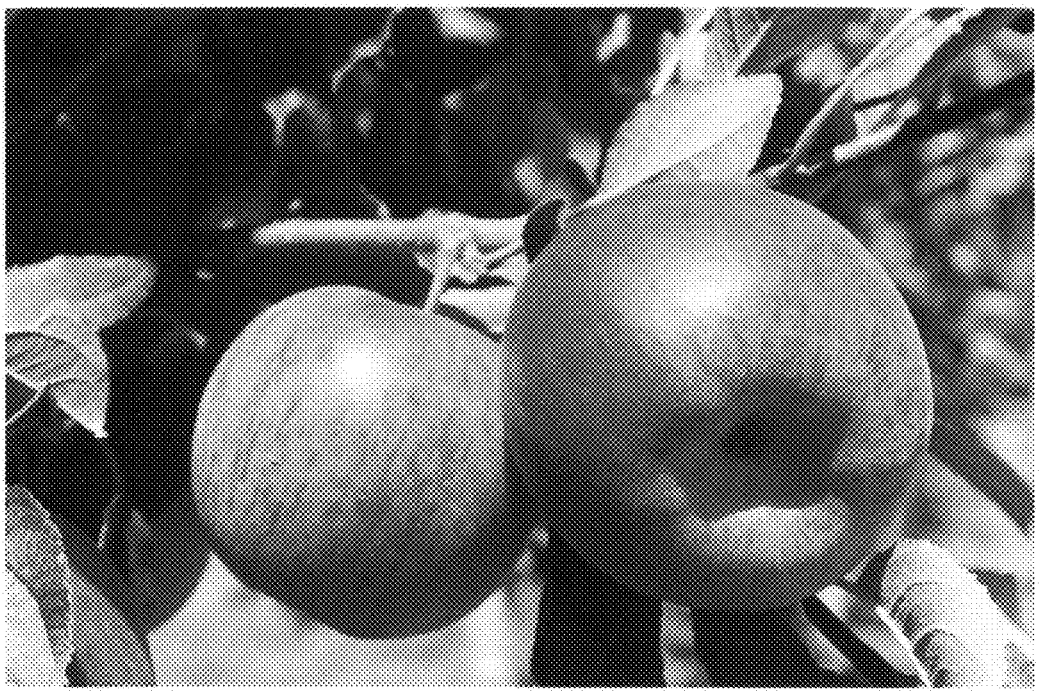

FIG. 1 shows the blossoms of 'PremA17'; and
FIG. 2 shows the fruit of 'PremA17'.

DETAILED BOTANICAL DESCRIPTION

The following detailed botanical description is based on observations of three year old 'PremA17' apple trees grown at Havelock North, New Zealand. Color descriptions refer to The Royal Horticultural Society Colour Chart, published in 2001. It should be understood that the characteristics described will vary somewhat depending upon cultural practices and climatic conditions, and can vary with location and season. Quantified measurements are expressed as an average of measurements taken from a number of individual plants of the new variety. The measurements of any individual plant, or any group of plants, of the new variety may vary from the stated average.

Tree:
- *Vigor.*—Medium vigor.
- *Habit.*—Spreading.
- *Bearing.*—Spurs and long shoots.
- *Size.*—Height: 1.8 m; spread 1.0 m.
- *Trunk.*—Diameter; 2.5 cm at 30 cm above graft union; bark texture smooth; color greyed-orange 176B.
- *Trunk lenticels.*—Density 40 per square inch; length 0.1 to 0.2 cm; color orange-white 159D.
- *Branches.*—Length 60 cm; diameter 0.9 cm; crotch angle 90°; color greyed-orange 176B (fruiting branch located about 1 m above graft union).
- *Branch lenticels.*—Density 15 per square inch; length 0.1 cm; color orange-white 159D.
- *Winter hardiness.*—Hardy in Hawkes Bay, New Zealand.

Dormant one year old shoot:
- *Size.*—Diameter 0.5 cm; length 47 cm.
- *Color.*—Brown N200C over greyed-orange 176B.
- *Internode length.*—2.5 cm.
- *Lenticels.*—Density 15 per square inch; length 0.1 cm; color orange-white 159D.

Flowers:
- *Bud.*—Quantity per spur 5 to 8; length 1.1 cm; diameter 0.8 cm; color red-purple N57D with white 155C.
- *Petals.*—Quantity per flower 5; Free, not touching; color white 155C and red purple N57D when fully open.
- *Flower.*—Diameter 5.2 cm.
- *Sepals.*—Quantity per flower 2; length 0.8 cm; width 0.2 cm; color yellow-green 144D.
- *Pedicel.*—Length 2.5 cm; diameter 0.2 cm; color yellow-green 144B.

*Anthers.*—Quantity per flower 10; length 0.1 cm; pollen color yellow 4C.
*Stigma.*—Color yellow 4C.
*Style.*—Length 0.9; color yellow 145B.
*Ovary.*—Length 0.5 cm; width 0.2 cm; color yellow-green 145B.
*Time of flowering.*—Last week of September in Hawkes Bay, New Zealand.
*Pollination requirement.*—No special pollination requirements known.

Leaf:
*Size.*—Length 3.2 cm; width 1.2 cm.
*Margin.*—Serrate.
*Surface texture.*—Upper surface medium glossy; Lower surface weak pubescent.
*Color.*—Upper surface green 137B; lower surface yellow-green 146C.
*Shape.*—Ovate; apex acuminate; base equilateral.
*Petiole.*—Length 1.5 cm; width 0.3 cm; color yellow-green 144D.

Fruit:
*Size.*—Diameter 7.6 cm; height 7.6 cm.
*Fruit shape.*—Globose.
*Position of maximum diameter.*—Equator.
*Ribbing.*—Absent.
*Crowning at calyx end.*—Absent.
*Aperture of eye.*—Closed.
*Depth of eye basin.*—Medium, 1 cm.
*Width of eye basin.*—Medium, 2.5 cm.
*Lenticels.*—Medium, diameter 1 mm; Density 5 per $cm^2$.
*Locule.*—Aperture of locule in transverse section partly open; Average size of locule is 8.6 mm by 4.8 mm.
*Stalk.*—Diameter 0.5 cm; length 4.0 cm.
*Depth of stalk cavity.*—Medium, 1.8 cm.
*Width of stalk cavity.*—Medium 1.5 cm.
*Size of lenticels.*—Very small. 0.5 mm.
*Bloom of skin.*—Absent.
*Greasiness of skin.*—Absent.
*Ground color of skin.*—Yellow 3C.
*Over color of skin.*—Red 45A stripe with red 47B blush over approximately 25% of surface.
*Flesh.*—Texture crisp; medium juiciness; color white 155B.
*Seeds.*—Quantity per fruit 5; teardrop shape; length 0.7 cm, width 0.5 cm; color greyed-orange 166A.
*Aroma.*—Weak.
*Harvest date.*—2 weeks before 'Tenroy Gala' (U.S. Plant Pat. No. 4,121).
*Storage.*—Fruit remains in good condition after 70 days in storage at ±0.5° C.
*Disease/pest resistance.*—None observed.
*Market use.*—Dessert.

I claim:

1. A new and distinct variety of apple plant substantially as shown and described herein.

* * * * *